United States Patent [19]

Braquet et al.

[11] Patent Number: 4,904,693
[45] Date of Patent: Feb. 27, 1990

[54] OCTAHYDRO INDENOFURAN DERIVATIVES AND THEIR THERAPEUTIC COMPOSITIONS

[75] Inventors: Pierre Braquet, Garches; André Esanu, Paris, both of France

[73] Assignee: Societe de Conseils Recherches et d'Applications Scientifiques, France

[21] Appl. No.: 267,438

[22] Filed: Nov. 4, 1988

[30] Foreign Application Priority Data

Nov. 4, 1987 [GB] United Kingdom ............... 8725872

[51] Int. Cl.$^4$ ............................................. C07D 307/92
[52] U.S. Cl. ..................................... 514/468; 549/299
[58] Field of Search ......................... 549/299; 514/468

Primary Examiner—Jane T. Fan
Attorney, Agent, or Firm—Lucas & Just

[57] ABSTRACT

This invention relates to indenofuran derivatives of the formula:

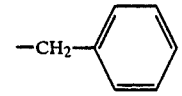

wherein R stands for H or for a

—CH$_2$—⌬ group optionally substituted on the phenyl ring by Alk, OH or OAlk, Alk being a lower straight or branched alkyl group up to C$_5$, to the preparation of these compounds and to therapeutic compositions containing the same in the field of anaphylaxis.

2 Claims, No Drawings

OCTAHYDRO INDENOFURAN DERIVATIVES AND THEIR THERAPEUTIC COMPOSITIONS

The invention relates to indenofuran derivatives, to a method for their preparation and to therapeutic compositions containing the same.

The invention provides octahydro-indeno [7,7a,1-bc]furan-2,3-dione derivatives of the formula:

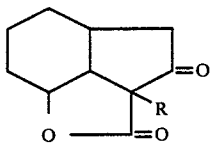

wherein R stands for H or for a

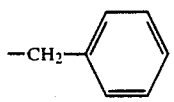

group optionally substituted on the phenyl ring by Alk, OH or OAlk (Alk is a lower straight or branched alkyl group up to $C_5$).

The invention further provides a method for the preparation of octahydro-indeno [7,7a,1-bc]furan-2,3-dione (R=H), the method comprising reacting 1,2,3,4-tetrahydrophenylacetoacetic acid with manganese acetate in the presence of an excess of acetic acid and acetic anhydride and, when R is not hydrogen, a method for subsequently preparing the desired compounds by condensing the previously obtained compound on Br R, under nitrogen circulation, at a temperature between $-10°$ and $0°$ C. in the presence of sodium hydride.

The compound according to the invention is useful as a precursor for the synthesis both of Ginkgolides and of related derivatives presenting a PAF-Acether antagonist activity. Most of these compounds present also per se an interesting therapeutic activity in the field of anaphylaxy.

The following examples illustrate the invention:

EXAMPLE 1

2a,4,4a,5,6,7,7a-octahydroindeno 7,7a,1bc furan - 2,3-dione 200 ml of acetic acid, 10 ml of acetic anhydride and 20.1 g (0.075 mol) of $Mn(OCH_2CH_3)_3 \cdot 2H_2O$ were poured, under nitrogen circulation, into a reactor fitted with warming, cooling and stirring means. The reaction mixture was warmed to 70° C. and stirred. After cooling to room temperature, there was added under stirring, 5.5 g (0.03 mol) of 1,2,3,4-tetrahydrophenylacetoacetic acid. Stirring was maintained for 20 minutes at room temperature, under nitrogen circulation after which the reaction mixture was poured onto ice, then extracted twice with 250 ml of $CH_2Cl_2$. After washing the organic phases with water, and drying, there was obtained, after treatment on a silica gel column (eluent, ethyl acetate : hexane 2:1 by volume), 3 g (yield 55.4%) of a powder. Elemental analysis showed a very good correspondence with the formula $C_{10}H_{12}O_3$; the structure was confirmed by HPLC.

EXAMPLE 2

2a,4,4a,5,6,7,7a-octahydroindeno 7,7a,1bc, furan-2a-(2-methoxy benzyl)-2,3-dione In the same apparatus as above were poured 100 ml of tetrahydrofuran and 2.1 g (0.0117 mol) of the compound of example 1 and the mixture was cooled at $-5°$ C. There was then slowly added under stirring, 0.735 g (0.0175 mol) of NaH (title 59%, in oil). Stirring was maintained for 30 minutes. There was thus added, dropwise 5.85 g (0.030 mol) of 2-methoxy benzyl bromide. Under gentle stirring for 3 hours the temperature was allowed to reach slowly 0° C. The reacting mixture was then poured on 100 ml of iced HCl N. After extraction by ethyl acetate, washing with water, drying, the residue is chromatographied on a silica gel column (eluent ethyl acetate/hexane 4/6 in vol.). The title compound was thus obtained (yield 23.5%). This was a white powder melting at 142° C. (Tottoli) the analysis of which showed a perfect correspondence with the formula $C_{18}H_{20}O_4$.

By the same method were also prepared:

EXAMPLE 3

2a,4,4a,5,6,7,7a-octahydroindeno 7,7a,1bc, furan - 2a-(2-ethoxy benzyl)-2,3-dione White powder melting at 168° C. (Tottoli), the analysis of which showed a perfect correspondence with the formula $C_{19}H_{22}O_4$.

EXAMPLE 4

2a,4,4a,5,6,7,7a-octahydroindeno 7,7a,1bc, furan - 2a -benzyl-2,3-dione

White powder melting at 173° C. (Tottoli), the analysis of which showed a perfect correspondence with the formula $C_{17}H_{18}O_3$.

EXAMPLE 5

2a,4,4a,5,6,7,7a-octahydroindeno 7,7a,1bc, furan - 2a-(3-hydroxy benzyl)-2,3-dione White powder melting at 131° C. (Tottoli), the analysis of which showed a perfect correspondence with the formula $C_{17}H_{18}O_4$.

EXAMPLE 6

2a,4,4a,5,6,7,7a-octahydroindeno 7,7a,1bc, furan - 2a-(3-hydroxy-4-methoxy benzyl)-2,3 dione White powder melting at 107° C. (Tottoli), the analysis of which showed a perfect correspondence with the formula $C_{18}H_{20}O_5$.

EXAMPLE 7

2a,4,4a,5,6,7,7a-octahydroindeno 7,7a,1bc, furan - 2a-(4-terbutyl benzyl)-2,3-dione White powder melting at 187° C. (Tottoli), the analysis of which showed a perfect correspondence with the formula $C_{21}H_{26}O_3$.

TOXICITY

The toxicity was determined per os on rats and mice by the usual methods. $DL_{50}$ was always over 1 g/kg for rats and over 700 mg/kg for mice.

PHARMACOLOGY

A proof of the pharmaceutical interest of the compounds of the invention has been established by the following pharmaceutical experimentations:

(1) Test of Passive Cutaneous Anaphylaxy (PCA) on the Rat Associated With Hyperpermeability to PAF or to Histamine This experiment was conducted as described in "Fiche Technique N° 48 of J. Pharm. Paris 1979 10 (1) pages 69–72 (adaptation of the method of BITTEAU E. and HERTZ F.). The method is summarized as follows:

Male Sprague-Dawley rats (180–200 g) - six animals per batch. Eight batches were used: one for control, one for each of the example compounds, at the dose of 25 mg/kg.

In two sites of the back, previously shaved, were made two injections of an homologous immune-serum (0.1 ml) diluted for a quater.

48 hours later, the rats were submitted to a control and received an intravenous injection of 1 ml of a mixture of ovalbumine (0.5%) and Evans blue (0.5%), in physiologic serum. As a consequence, the formation of the IgE-antigen complex induced the exsudation of plasmatic proteins and the formation of cutaneous wheals, this phenomenon being quantified measuring their surface (S) and their coloration (after extracting for 24 hours in a formamide solution at 65° C.): Optical density of the supernatant was determined at 620 nm by a spectrophotometer.

The animals were kept fasting for 18 hours before the control. The products were administered, by IP route just before the administration of colorant.

Just before the IV injection of colorant, all the animals, including those of control batch, received two intra-dermal injections, in two sites of the back, of PAF (0.025 mcg/0.1 ml) or histamine, opposed to the injections of immune-serum.

30 minutes later, the induced wheals were treated as the wheals obtained with immune-serum.

The results are appreciated by the percentage of variation of optical density with respect to control.

The corresponding values appear in the following table.

| COMPOUNDS | PAF AREA | PAF COLOUR | HISTAMINE AREA | HISTAMINE COLOUR |
|---|---|---|---|---|
| EX. 1 | −46.4*** | −50.5*** | −23.5* | −18.7 NS |
| EX. 2 | −57.1*** | −61.2*** | −18.0 NS | −17.7 NS |
| EX. 3 | −39.4** | −44.4*** | −26.8* | −23.4* |
| EX. 4 | −43.6*** | −51.7*** | −36.8** | −39.9*** |
| EX. 5 | −36.6** | −43.8** | −16.2 NS | −17.9 NS |
| EX. 6 | −50.9*** | −62.7*** | −43.9*** | −36.8** |
| EX. 7 | −42.1** | −53.5*** | −13.7 NS | −18.4 NS |

NS: non significative
*significative
**very significative
***highly significative (2) Anaphylactic Bronchoconstriction of a Passively Sensitized Guinea-pig

Passive Heterolog Sensitizing

Male Hartley guinea-pigs (400–500 g) were sensitized by an intravenous injection (IV) of an antiovalbumin rabbit immune-serum (Cooper Biomedical, U.S.A.). To obtain a satisfactory anaphylactic response, 24 hours later, the following conditions of use were fixed: injection into the penis of a diluted serum (to half concentration; 0.05 ml/100 g).

Bronchoconstriction Measure

Guinea-pigs were anesthetized with urethan (2 g/kg IP) then tracheotomized and ventilated by mean of a respiratory pump (UGO BASILE): stroke volume 1 ml/100 g, 60 strokes/mn. A pneumothorax was done to abolish spontaneous respiration. The initial resistance was kept constant at 10 cm water pressure according to the method of Konzett and Rössler and the excess of air volume was measured with a bronchospasm transducer (UGO BASILE) connected to a UGO BASILE recorder "Gemini". The jugular vein was catheterized for intravenous injections. The anaphylactic shock was induced by an intravenous injection of 0.75 mg/kg of heterolog passive of ovalbumine. Products were given by oral route, 1 hour before the antigenic stimulation in the forma of a gummy water suspension at the dose of 25 mg/kg.

Results

The bronchoconstriction induced by ovalbumin was expressed in percentage of maximal bronchoconstriction given by clamping of the trachea. The results are reported in the following table.

| EXAMPLES | PERCENTAGE OF REDUCTION OF BRONCHOCONSTRICTION |
|---|---|
| 1 | 53.2*** |
| 2 | 49.8*** |
| 3 | 63.7*** |
| 4 | 58.3*** |
| 5 | 41.4** |
| 6 | 55.9*** |
| 7 | 48.6*** |

**very significative
***highly significative

Posology

In human therapy usual doses for per os administration are 0.5 to 1 g per diem, in tablets or gelatine capsules for one month. In IV administration, three weekly injections at 0.05 to 0.2 g in isotonic solution, for one month are recommended.

We claim:

1. Indenofuran derivatives of the formula:

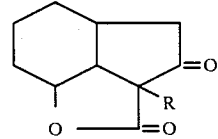

wherein R stands for H or for a

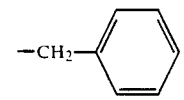

group optionally substituted on the phenyl ring by Alk, OH or OAlk, Alk being a lower straight or branched alkyl group up to $C_5$.

2. A therapeutic composition of matter for anaphylaxis containing, as an active ingredient therein, a sufficient amount of a compound according to claim 1, together with an appropriate diluent or carrier.

* * * * *